United States Patent [19]

Walz, Jr. et al.

[11] 4,230,115
[45] Oct. 28, 1980

[54] CATHETERIZATION UNIT

[75] Inventors: Arthur J. Walz, Jr., Elk Grove Village; Christopher A. Nowacki, Des Plaines, both of Ill.

[73] Assignee: Illinois Tool Works Inc., Chicago, Ill.

[21] Appl. No.: 953,336

[22] Filed: Oct. 20, 1978

Related U.S. Application Data

[63] Continuation-in-part of Ser. No. 831,702, Sep. 12, 1977, abandoned.

[51] Int. Cl.³ .............................................. A61F 5/44
[52] U.S. Cl. ............................. 128/295; 128/DIG. 9; 128/DIG. 24; 128/349 R; 128/768; 206/364; 206/438
[58] Field of Search ............... 206/364, 363, 438, 484, 206/620; 222/530, 541; 128/DIG. 9, DIG. 24, 295, 294, 349 R, 227, 276, 750, 760, 761, 765, 766, 767, 768, 772

[56] References Cited

U.S. PATENT DOCUMENTS

| 2,789,734 | 4/1957 | Biederman | 222/530 |
|---|---|---|---|
| 2,856,932 | 10/1958 | Griffitts | 128/294 |
| 2,883,985 | 4/1959 | Evans | 128/295 |
| 2,936,757 | 5/1960 | Trace | 128/276 |
| 2,976,988 | 3/1961 | Schneider | 206/484 |
| 3,112,031 | 11/1963 | Stewart | 128/349 R |
| 3,364,932 | 1/1968 | Beach | 128/295 |
| 3,473,532 | 10/1969 | Eisenberg | 128/295 X |
| 3,648,704 | 3/1972 | Jackson | 128/349 R |
| 3,742,523 | 7/1973 | Atkins | 128/295 |
| 3,841,332 | 10/1974 | Treagle | 128/295 |
| 3,888,235 | 6/1975 | May et al. | 128/295 |
| 3,888,236 | 6/1975 | Marx | 128/295 |
| 4,029,099 | 6/1977 | Fifield | 128/295 |

FOREIGN PATENT DOCUMENTS

| 960931 | 1/1975 | Canada | 128/295 |
|---|---|---|---|
| 2249132 | 4/1973 | Fed. Rep. of Germany | 128/295 |
| 2435288 | 2/1976 | Fed. Rep. of Germany | 128/295 |
| 2634567 | 7/1976 | Fed. Rep. of Germany | 128/295 |
| 871862 | 5/1961 | United Kingdom | 128/295 |
| 1232763 | 5/1971 | United Kingdom | 128/295 |

*Primary Examiner*—Robert W. Michell
*Assistant Examiner*—J. L. Kruter
*Attorney, Agent, or Firm*—J. R. Halvorsen; T. W. Buckman

[57] ABSTRACT

An aseptic urethral catheterization unit including an elongated initially sealed flexible plastic container sealed at all edges and including a restricted medially disposed opening spaced from one end of the container. An imperforate rupturable means positioned between the restricted opening and the one end of the container to permit ready access to a small chamber formed in said container adjacent the restricted opening. A urethral catheter positioned initially within a second chamber in the container and rigid tubular catheter guide means positioned within said restricted opening. The guide means includes means permitting intermittent grasping of the catheter as it is fed out of the container after breakage of the frangibly connected sealed end portion of the container.

33 Claims, 21 Drawing Figures

CATHETERIZATION UNIT

This is a continuation-in-part of application Ser. No. 831,702 filed Sept. 12, 1977, now abandoned.

BACKGROUND OF THE INVENTION

This invention relates generally to fluid connectors for use with catheters and related apparatus, and more particularly concerns a catheter fluid collector device which can be maintained in a substantially aseptic condition prior to and during useage. Many victims of paralysis are unable to voluntarily evacuate their bladder. These persons must be catheterized periodically in order to remove accumulated body waste fluids.

A number of non-surgical and semi-surgical techniques and related devices have been offered to perform this catheterization. For male patients this procedure in general involves aseptically preparing the penis, then inserting a catheter into the urethra, while maintaining sterile technique, until the eye of the catheter reaches and communicates with the bladder. Urine then flows through the catheter and can be directed into a collection container or disposal device. Such techniques normally require skills and training only available in professional personnel such as medical doctors and/or registered nurses including the high rate of economic obligations incurred through the use of such services. Even with such skilled help, some of these techniques and their associated implements offer the dangers of urethra contamination during procedure preparation, catheter contamination during handling, and specimen contamination during specimen container filling, sealing and emptying. Most of the techniques in associated apparatus must be performed in a semi-surgical setting; they cannot be conveniently performed by the patient himself while he is alone and in a semi-private washroom or other location.

When collector bags or receptables are provided, some catherization apparatus permit inadvertent removal of the catheter from the collector, thus presenting the possibility of accidental spillage and attendant mess. Such an occurrence can cause discomfort and even humiliation to the patient.

SUMMARY OF THE INVENTION

It is accordingly the general object of the present invention to provide a urine collector which is handy and safe to use, can be maintained in aseptic conditions prior to useage and which, in the preferred embodiment, involving a flexible plastic collector container, will provide a readily available chamber for acceptance of the glans of a male penis for immediate locating of the penis relative to the aseptically contained urethral catheter for insertion into the urethra.

It is a further object of the invention to provide a urine collector and catheter device which minimizes the danger of catheter contamination during catheter insertion into the urethra by permitting such catheter insertion without the catheter being directly touched or handled at any time.

An associated object is to provide such a collector and catheter which encourages and maximizes the maintenance of sterile technique.

Still another object is to provide a collector and catheter which can be used with relative ease even by relatively inexperienced personnel, such as the patient himself when he is alone in a washroom or relatively private area. An associated object is to provide such a collector and catheter which, when used by the patient himself with a minimum of instruction, will thereby reduce the professional time and final medical expense.

Yet another object of the invention is to provide such a collector and catheter which can be manufactured, packaged and commercially offered at an economical cost.

Other objects and advantages in the invention will become apparent upon reading the following detailed description with reference to the drawings. Throughout the drawings, like reference numerals refer to like parts.

DETAILED DESCRIPTION OF THE INVENTION

While the invention will be described in connection with preferred embodiments and procedures, it will be understood that it is not intended to limit the invention to these embodiments or procedures. On the contrary, it is intended to cover all alternatives, modifications and equivalents as may be included within the spirit and scope of the invention and defined by the appended claims. For example, this collector device and procedure can be used, with suitable modifications, by female as well as male patients.

Figure 1:
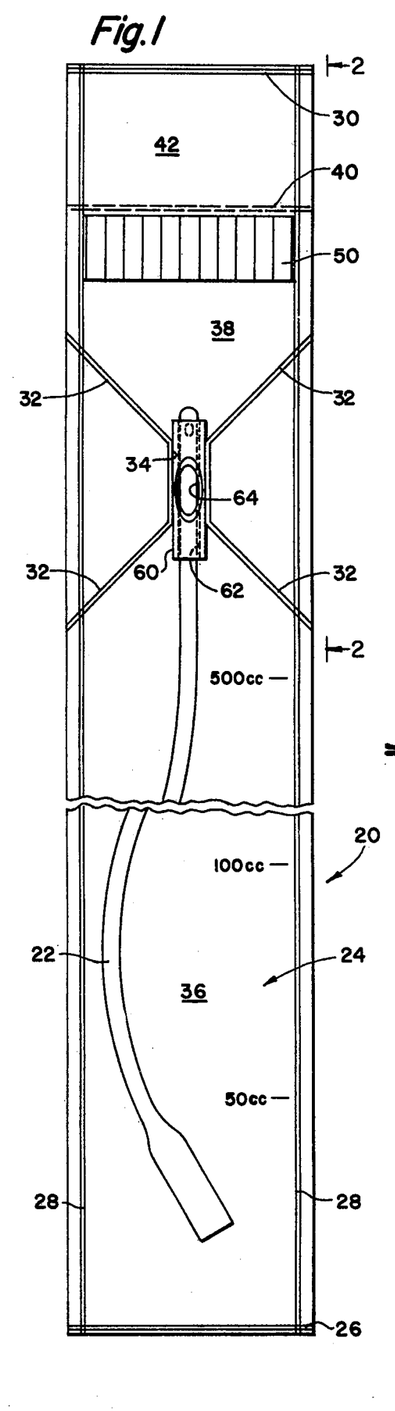
FIG. 1 is an elevational view in partial section of a preferred embodiment of the present invention showing the novel collector container and catheter in sealed condition.

Referring now to FIG. 1, a novel collector of the type embodying the present invention includes a container 20 and a catheter 22. The container preferably takes the form of a transparent elongated flexible bag 24 made of a suitable thermoplastic material such as polyethylene, polypropylene, cellulose acetate, vinyl resins such as polyvinylidene chloride, polyvinyl chloride, polyvinyl acetate and their mixtures or co-polymers and the like film forming resin materials, capable of forming sealed packages produced therefrom. The bag 14 can be of an elongated form, as illustrated, and is defined by two folded or otherwise opposed material layers of film sealed at the bottom 26, along the opposed edges 28, and at the upper end 30 to provide an imperforate sealed package. It is contemplated that the bag interior will be rendered sterile by appropriate known procedures either before or after sealing all sides and ends thereof. The sealing of thermoplastic materials can be accomplished by known heat sealing, sonic welding, or adhesive means.

The bag or container 24 is provided intermediate its length with a pair of truncated chevrons 32 with their truncated portions spaced from one another to form a restricted medially disposed opening 34 that provides communication between a large lower chamber 36 which initially houses the catheter 22 and a smaller funnel-shaped chamber 38 adjacent the opposite end 30. The upper end of chamber 38, as viewed in the drawings, is defined by a transverse frangible weakened portion 40 spaced from the sealed end 30 a distance sufficient to provide a grippable portion 42 that will permit the user to grasp the bag on either sides of line 40 and by ripping or tearing to break the sealed aseptic condition of the container 24 and to expose the open mouth of chamber 38. As one example of a means of providing an imperforate sealed package having this frangible connection see U.S. Pat. No. 3,186,628 issued to William A. Rohde on June 1, 1965. The rupturable envelope described in that patent with its relatively thinned groove line in the body portion is ideally adapted for use in the present invention. However, other forms of providing access to a thermal plastic container can be adapted to this invention as long as the container remains imperforate and sealed prior to rupturing along the predetermined line.

Figure 3:
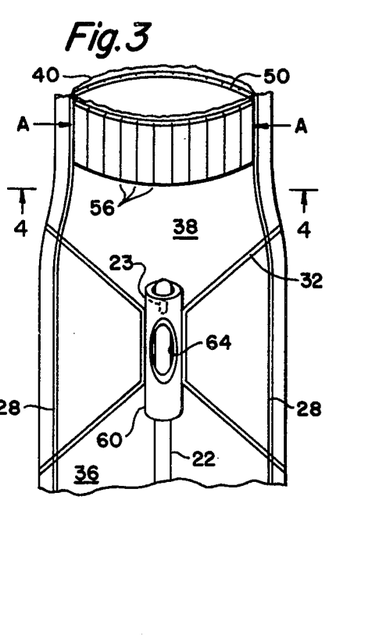
Figure 4:
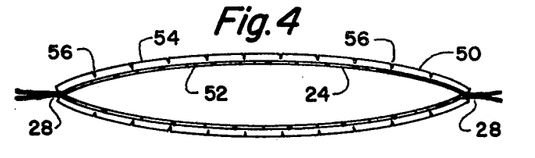
FIG. 4 is a sectional view taken along Line 4—4 in FIG. 3.
Figure 5:
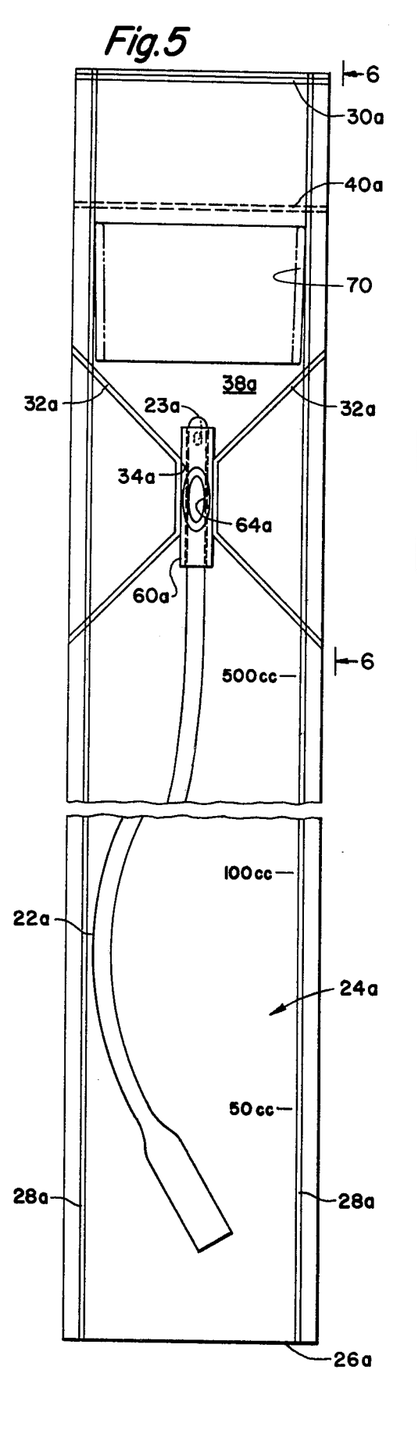
FIG. 5 is an elevational view of a second embodiment of the invention showing a different form of opening device for creating the first chamber in the collector container.
Figures 6, 7:
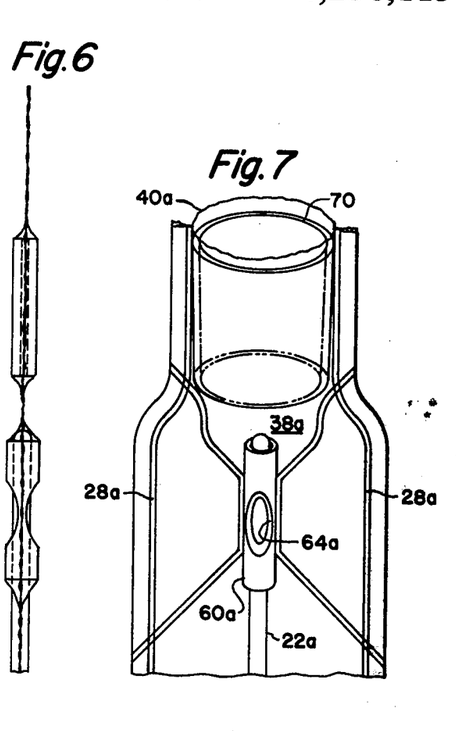
FIG. 6 is a partial side elevational view of the container shown in FIG. 5 and as viewed along Lines 6—6 of FIG. 5.
FIG. 7 is a partial perspective view of the device shown in FIGS. 5 and 6 when the rupturable portion of the container has been removed and the catheter is in position for insertion in the urethra.
Figure 8:
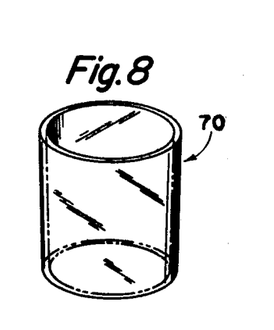
FIG. 8 is a perspective view of an expander element of the type used in FIGS. 5 through 7.

Since the container 24 is a flexible thin walled thermoplastic sheet material, this invention contemplates the use of an opening device 50 positioned at the upper end of chamber 38 adjacent to the frangible line 40 and extending substantially transversely of the container 24 between opposite sealed edges 28. In this embodiment the opener 50 includes a pair of substantially flat thermoplastic elements having a smooth substantially continuous surface 52 which is positioned adjacent the outer surface of the container 24 and affixed thereto by suitable means such as adhesives, sonic welding or heat sealing, throughout substantially its entire extent. The opposite surface 54 is provided with a plurality of slits 56 which extend axially relative to the container and completely from edge to edge of the strip 50. The slits 56 extend through a substantial portion but not completely through the strip 50. As illustrated in FIG. 4, a pair of these strips are used; and when a force, designated by the arrows AA in FIG. 3, is applied to the edges 28 of the container 24, the strip 50 facilitates the bowing open of chamber 38 into a substantially open-throated condition having a funnel-shape at the base or lower end of the chamber 38 as viewed in the drawings and as seen in FIG. 3. This provides ready access to the upper chamber for insertion and location of the penis glans within the chamber 38 and with the urethra aligned with the restricted opening 34.

Figure 2:
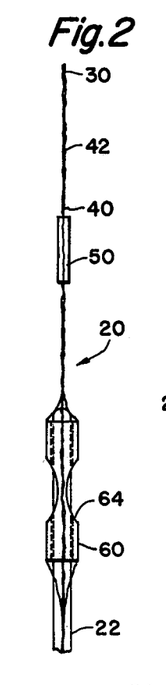
FIG. 2 is a partial side elevational view similar to FIGS. 1 and 2 but showing the container with one end unsealed and the catheter as it would appear when it is being inserted into the urethra.

To assist with the manipulation of the catheter 22, the restricted opening 34 is provided with a substantially rigid tubular guide means 60 having a hollow bore 62 throughout its extent with an internal diameter equal to or greater than the diameter of the catheter 22 to permit ready access therethrough. As can be appreciated, the use of a lubricious material will readily assist the threading of the catheter through the guide means 60. To further assist in the manipulation of the catheter during its insertion in the urethra, the guide means 60 includes one or more port means 64 opening through the side wall of the guide means 60 and communicating with the internal bore 62. In the preferred embodiment, as illustrated, the port means 64 is an oval aperture having the walls of the guide means 60 concavely disposed in a radial direction, as best seen in FIG. 2. The lowest point of the walls forming the port means 64 are closer to the opposite wall of the bore 62 then the diametral measurement of the catheter 22. This permits the user, operating through the flexible walls of the container 24, to grip the catheter. To further enhance such gripping, the preferred embodiment shows a pair of port means opening through opposite walls of the guide means 60, as best seen in FIG. 2. This permits the user to grip the catheter through the flexible walls of container 24 and to hold the catheter in the predetermined axial position relative to the guide means, for purposes best set forth hereinafter.

In the use of the present device, the patient himself or with professional assistance would sterilize the glans of the penis and the adjacent area. The sealed container 24 would then be ruptured along line 40 and a force applied in the direction of the arrows A, as seen in FIG. 3, to open the upper end of chamber 38. A sterile lubricant, such as a petroleum jelly base substance, now shown, would be placed into chamber 38 and would be collected in the lower funnel portion formed by the chevrons 32 adjacent the guide means 60. The glans of the penis are then inserted into chamber 38 with the urethra aligned semi-automatically with the bore 62 of the guide means 60. Movement of the catheter axially upwardly, as viewed in the drawings, would result in the catheter being coated by the lubricant placed in the reservoir formed by chamber 38 and the catheter fed upwardly by flexing the container 24. By gripping the catheter through the port 64, the bag can then be extended to its initial position, the catheter re-gripped and moved axially again with a secondary flexing of the bag. This operation is continued until the eye 23 of the catheter reaches the interior of the patient's bladder whence voiding is commenced. As illustrated, the container 24 is provided with volumetric indicia means along one edge thereof so that a patient can be voided to a predetermined extent. There are deleterious effects if the patient is totally voided and hence normally a predetermined amount of fluid is evacuated and thence the catheter removed. While there is some clearance between the outside wall of the catheter 22 and the internal wall of bore 62, it sometimes is desirable to feed the catheter downwardly within the container until the catheter 22 has cleared the bore 62 to provide a complete opening for evacuation of the container by inverting it over a suitable disposal means.

Referring now to FIGS. 5 through 8 wherein a modification of the present invention is illustrated and similar parts are referred to by similar numerals with the addition of the suffix "a", the catheterization unit again includes a flexible thermal plastic bag or container 24a housing a catheter 22a within aseptically sealed ends and edges 26a, 28a, and 30a respectively, and a pair of intermediate truncated chevrons 32a form a restricted opening 34a for acceptance of a guide means 60a. This device is also provided with a rupturable or frangible line 40 traversing the upper end adjacent end 30a for breaking the seal and providing access to the chamber 38a.

In the first embodiment disclosed, the opener means 50 included a pair of flexible slit members disposed in intimate contact with the outside surface of the bag and adapted to bow the opening defined by the frangible line 40. In the present instance, the opening means includes a tubular element 70 which is placed within the chamber 38, flattened to a compressed condition when the container 24a is sealed and having a memory characteristic such that when the seal is broken by rupturing along line 40a the cylindrical member 70 will return substantially to its initial position to bow the flexible sheet container outwardly to form a ready access to chamber 38a. Preferably the tubular element 70 is a clear thermoplastic material having rounded edges to avoid injury to the penis glans when inserted therein. The operation of this device is substantially identical in useage to the first embodiment except that this device eliminates the necessity of grasping the edges of the container and applying a force thereto. As will be apparent, some patients do not have the ability to provide such force factor and hence the tubular element 70, disposed in chamber 38a, provides an automatic opening or bowing of the throat formed along line 40a after fracture of the sealed condition of the device.

In the previous embodiments of the art, there has been some difficulty experienced in that the weight of the catheter 22 has a tendency to cause it to fall to the bottom of the chamber 24. The operator then has dificulty in respositioning the distal end or eye 23 of the catheter within the guide 60 for introduction into the patient's urethra. Additionally, the container formed by bag 20 is normally folded upon itself during packaging. If the catheter is not properly positioned during the bag folding operation it can be kinked when stored for prolonged periods thereby causing the catheter to be obstructed in its passageway and inoperative for its intended use.

Figure 9:
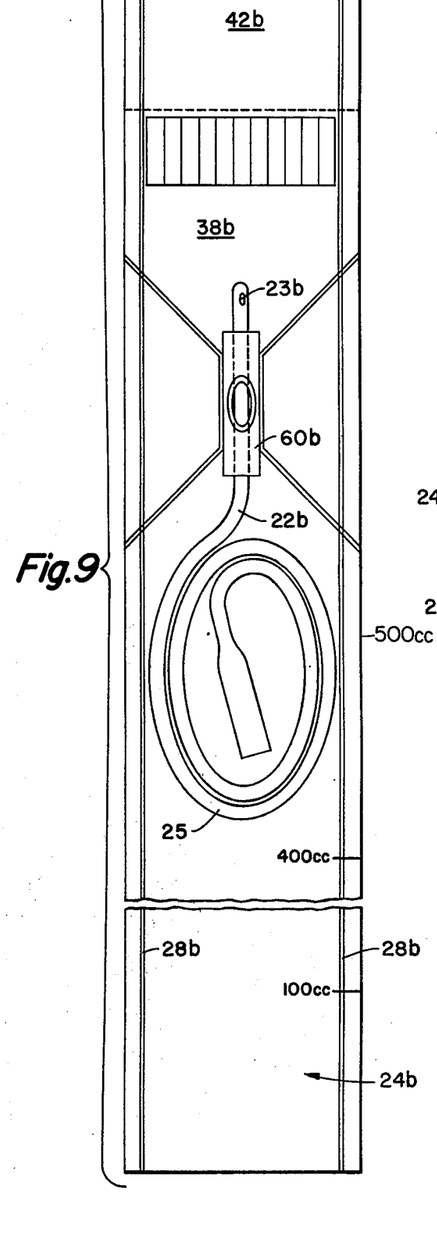
FIG. 9 is an elevational view of an embodiment, similar to FIG. 1, in which the catheter is maintained in the guide in a position of ready insertion by utilizing the spring nature of the catheter in coiled form to prevent it dropping to the bottom of the collector container.
Figure 10:
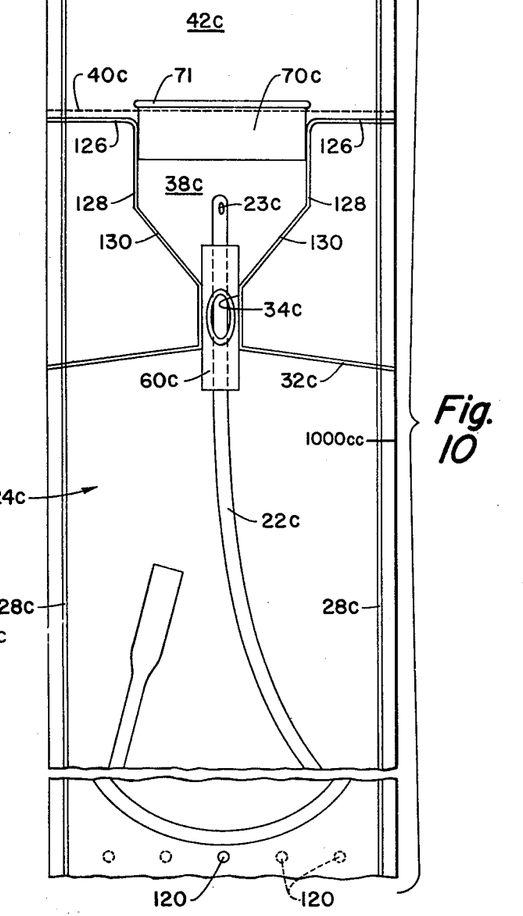
FIGS. 10, 10a and 10b are partial elevational views of means for maintaining the catheter within the guide means in a larger collector container plus a variation on the first chamber configuration.
Figure 10A:
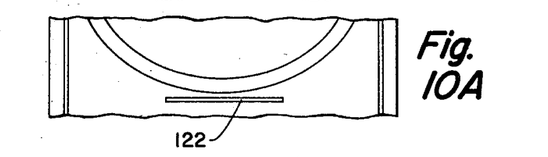
Figure 10B:
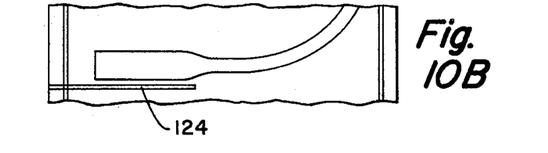

Two solutions to this problem have been proposed, the first being applied to narrow bags, as seen in FIGS. 1 through 9, and the second being used in wider bags, as seen in FIGS. 10,10A and 10B, having a much greater volumetric capacity.

Referring now to FIG. 9, wherein similar numerals are utilized to designate similar parts with the addition of the suffix "b", the natural resiliency of the rubber catheter 22b is utilized to form a spring-like coil 25 which reacts against the heat-sealed side walls 28b. This spring-like force is adequate to maintain the catheter 22b in a predetermined axial location within bag 24b and thereby insure maintenance of the distal end or eye 23b within guide 60b. Movement of the catheter 22b through guide 60b readily results in an uncoiling of coil 25 during introduction of the catheter 22b into the patient's urethra. It also limits the overall packaged length of the catheter so that the balance of the container bag 24b may be appropriately folded for minimal space packaging.

The second solution to the problems of dripping and kinking catheters is shown in the embodiments shown in FIGS. 10, 10A and 10B, wherein similar parts are designated by similar numerals with the addition of the suffix "c".

In most situations a standard length urethral catheter is utilized in kits of the type contemplated, such catheters being approximately 41 cm. in overall length. It will be appreciated that where a predetermined length standard catheter is utilized it would not have sufficient coiled resiliency to axially retain itself when used in a wide bag 24c, as opposed to the previous embodiment and bag 24b.

In these embodiments it has been found that providing obstruction means intermediate the ends of bag 24c will permit a partial coiling or looping of catheter 22c, without relying on engagement with the side walls 28c for purposes of maintaining axial location of the catheter 22c. In FIG. 10, one or more heat sealed dots 120 arrayed in spaced apart transverse relation are used. In FIGS. 10A and 10B, a line heat seal 122 and 124, respectively, are arranged medially in the first instance and to one side in the second instance. In all three of these forms the unheatsealed portion of the bag 24c permits free flow of fluid into the lower chamber or reservoir while still preventing dropping of the catheter from the desired location of its eye 23c, within the guide 60c for ready introduction into the patient's urethra.

An additional feature of the embodiment shown in FIG. 10, is the fact that chamber 38c is formed by heat-sealed lines 126, 128 and 130; with heat seals 128 serving to capture the expansion element 70c formed with a smooth thickened edge 71. Edge 71 serves to provide additional hoop strength and a smooth point of entry for the penis glans into chamber 38c which is exposed when portion 42c is removed by tearing or rupturing along weakened line 40c, as in the other embodiments.

Figure 11:
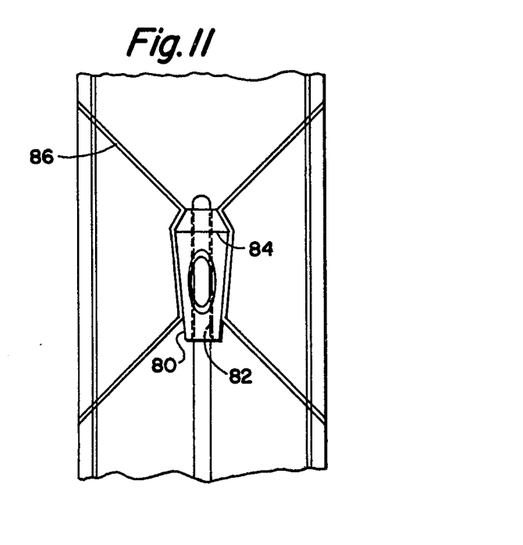
FIG. 11 is a partial elevational view of a further embodiment of a form of catheter guide which is axially captured within the collector container.

Referring now to FIGS. 11 through 17 wherein modifications to the guide means are illustrated, FIG. 11 discloses a guide means 80 having a central bore 82 and an external surface formed by two base oriented truncated cones forming an intermediate enlarged portion 84. The truncated chevrons 86 have their truncated portion conforming substantially to the external configuration of guide means 80 to thereby capture the guide means against axial movement relative to the container. Additionally, each of the catheters illustrated include an enlarged bulbous end opposite the end with the eye 23 and with the bulbous end having a larger diameter than the bore 82 it is virtually impossible for the catheter to be pulled out or through the guide means 80. This prevents the worrisome possibility of the patent dropping or losing the sample in the container by pull through of the catheter.

Figures 12, 13, 14, 15, 16, 17, 18, 19:
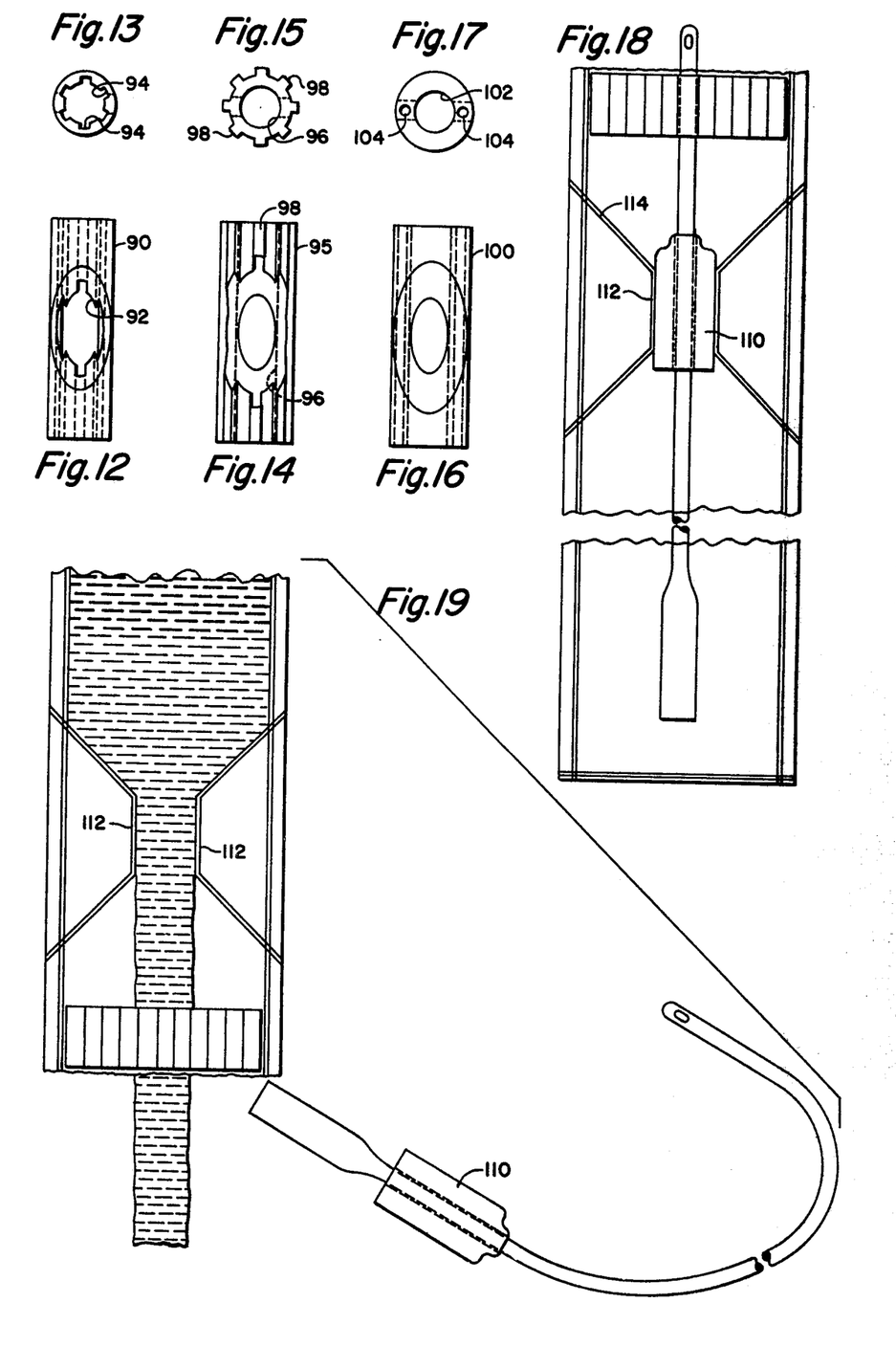
FIGS. 12 through 17 are elevational and end views of other embodiments of catheter guides when viewed before insertion into the collector container.
FIG. 18 is still another embodiment of the present invention with the rupturable portion removed, the catheter shown in extended positioned and a variation in catheter guide being illustrated.
FIG. 19 is an exploded view of the device shown in FIG. 16 after its chamber has been filled with urine, the catheter and catheter guide withdrawn and the contaner being in inverted position for discharge of the sample.

FIGS. 12 through 17 disclose modifications to the guide means for the purposes of providing higher flow rates than in the earlier embodiments. FIGS. 12 and 13 disclose a guide means 90 having gripping port means 92 similar to the other embodiments but additionally having internal splines or grooves 94 which provide clearance for the passage of fluids past the catheter that will be carried within the bore. The embodiment as shown in FIGS. 14 and 15 has a smooth internal bore 96 and external splines 98 for passage of excess fluid along the exterior surface thereof. The embodiment of guide means 100 shown in FIGS. 16 and 17 has a smooth exterior surface and a smooth interior bore 102 and is provided with one or more axially extending secondary passages 104 for providing additional fluid flow during evacuation of the container.

To further enhance the method of evacuation, the embodiment shown in FIGS. 18 and 19 includes a container substantially identical to the first embodiment shown in FIGS. 1 through 4 except in the design of the substantially rigid guide means, in this case designated by the numeral 110. In the previous embodiments the spacing between the truncated portion 112 of the chevrons 114 was equal to or less than the diameter of the bulbous end of the catheter. In this embodiment the external diameter of the guide means 110 is substantially greater than the bulbous portion of the catheter, and because of its oversized condition it is possible, by providing an axial stress on the catheter, to totally remove the guide means 110 and to utilize the total spacing between the truncated portions 112 of the chevrons to provide a large access or flow-through hole for evacuation of the sample, as best seen in FIG. 19.

It has also been found desirable to irrigate the bladder of certain patients after evacuation of the fluid specimen. This is particularly true in those situations where the patient is suffering either from inflammation, infection or other deleterious effects which can be best remedied by irrigation or by injection of a medicament directly into the bladder. To facilitate this, a catheterization unit of the types described hereinabove is utilized and while the catheter is implanted in the bladder of the patient, the penis is squeezed lightly to close the lumen of the urethra and thereby captures the catheter against axial displacement from its implanted position. While thus restraining the catheter, the rigid tubular guide is worked by finger manipulation in an axial direction so that it occupies the chamber 38 and is free of the restricted opening 34. In this position it is possible to extract the catheter with its bulbous end through the restricted opening 34. When this is accomplished, the container may then be evacuated, as shown in FIG. 19, and the catheter held steady, in implanted position, and a suitable syringe, not shown, inserted into the opening at the distal bulbous end of the catheter and thereby force the irrigation fluid through the catheter into the patient's bladder. Evacuation or removal of the irrigation fluid is then accomplished through the catheter into a secondary container, now shown. Utilization of this method described hereinabove permits evacuation of the bladder of a paralyzed patient by maintenance of the catheter in sterile condition within the bag during insertion through the urethra into the bladder, collection of the sample in the container, removal of the guide means and catheter from the interior and maintenance of an internal sterile condition in the catheter, subject only to the evacuation of the initial urine specimen, and followed by irrigation by suitable fluid means to alleviate bladder conditions being experienced by the patient.

Thus, the present invention contemplates an aseptically sealed container which can be economically fabricated from known materials to provide an aseptic urethral catherization unit consisting of a sealed imperforate container that remains in aseptic condition until immediately prior to useage either by the patient individually or with professional assistance. The thin flexible material forming the container is readily bowed into open mouth funnel-shaped condition presenting a first chamber for acceptance of the penis glans in an oriented relation with the urethra being substantially automatically positioned in line with the catheter fed through the rigid control means. This technique is fast and it has fewer steps than the known "open tray" kit approach because the concern about bladder infection is reduced since the catheter comes sealed in its own plastic, pouch-like container in such a way that the catheter itself is never touched. No draping is required; in fact, no drape, no gloves, no cotton balls, no forceps, no underpad and no specimen jar or plastic tray are needed. The present invention is self-contained in a neat pocket-size kit where everything needed to quickly perform the catheterization, measure the urine output and collect an uncontaminated specimen for the lab are all in the same unit. Additionally, a patient may be catheterized while sitting in a wheelchair. A supine position is not required with the present invention while such a supine position is virtually mandatory with present prior art techniques. The use of the present invention is so simple that the time required is reduced to under five minutes, which is about half the average time it takes to use an "open tray" kit as taught by the prior art. Modifications to the present invention will be apparent to those skilled in the art.

I claim:

1. An aseptic urethral catheterization unit including an elongated initially sealed flexible imperforate container, a urethral catheter having a predetermined diameter throughout a substantial portion of its length positioned in said container, said container including elongated flat flexible imperforate sheet material sealed about its entire perimeter in face to face relation, said container having a restricted portion forming a passageway spaced from one end thereof formed by sealing a limited area of said sheet material in face to face relation thereby creating a first chamber between said restricted portion and said one end, a second chamber substantially larger than said first chamber being formed between said restricted portion and said opposite end, substantially all of said catheter being initially positioned within said second chamber in an aseptic fashion but adapted for movement through said passageway upon manipulation externally of said container, said catheter having an eye adjacent one end communicating with the axial bore of said catheter, means for initially maintaining said eye end of said catheter substantially within said passageway which communicates between said chambers, and a transversely disposed weakened portion positioned between said one end and said restricted portion, said weakened portion having a generally linear configuration and existing in substantially aligned relation in each independent layer of said sheet material, said aligned portion extending substantially across the entire width of said container between opposite edges on a line spaced from said one end and said portion being manually separable along said line to break said seal upon manipulation and expose said eye end of said catheter and said first chamber in the interior of said container, said second chamber adapted for collection and acceptance of an aseptic specimen and aseptic initial storage of said catheter, whereby application of a surgical lubricant into said first chamber adjacent said restricted portion passageway substantially seals the juncture of said catheter and said passageway and protects said second chamber against external contamination.

2. A unit of the type claimed in claim 1 having catheter guide means disposed within said restricted portion, said guide means having a substantially rigid tubular configuration and adapted to accept said catheter for passage therethrough.

3. A unit of the type claimed in claim 2 wherein said guide means is a substantially rigid tubular member having port means intermediate its length and positioned adjacent at least one inner surface of said sheet material and which permits the catheter to be grasped through the walls of the container and port means as it is fed through the guide means.

4. A unit of the type claimed in claim 3 wherein said guide means includes a pair of port means opening through opposite sides of said guide means.

5. A unit of the type claimed in claim 3 wherein said port means includes an opening formed by axially disposed radially concavely shaped oval openings communicating through the walls in said cylinder, the lowest point of said wall measured from the oppositely disposed wall being less than the predetermined diameter of said catheter whereby said catheter can be gripped during extension and movement of said flexible container relative to said catheter during feeding of said catheter through said guide means.

6. A unit of the type claimed in claim 3 wherein said guide means is provided with axially extending channel means adapted to provide a fluid passageway.

7. A unit of the type claimed in claim 6 wherein said guide means includes axially disposed splines forming interdental fluid passageways.

8. A unit of the type claimed in claim 7 wherein said splines are externally disposed along said guide means.

9. A unit of the type claimed in claim 7 wherein said splines are internally disposed along said guide means.

10. A unit of the type claimed in claim 6 wherein said channel means includes at least one axially disposed secondary bore laterally spaced from the main cylinder bore.

11. A unit of the type claimed in claim 3 wherein said tubular member is cylindrical throughout its axial extent and has an internal bore greater than said predetermined catheter diameter, said catheter at one end having a bulbous terminal portion greater than said bore whereby axial stress on said catheter with said bulbous portion in contact with said guide means causes said guide means and catheter to be totally removed through said restricted portion to expose all of said passageway to fluid flow therethrough.

12. A unit of the type claimed in claim 3 wherein said container includes means intermediate its extremities for maintaining said catheter in a predetermined position within said second chamber.

13. A unit of the type claimed in claim 12 wherein the distance between the two edges of said container is predetermined and said catheter in coiled form reacts against said edges to prevent movement of said catheter away from said guide means.

14. A unit of the type claimed in claim 12 wherein said sheet material container is heat sealed by at least one small area intermediate the edges and opposite ends to restrict the axial positionment of said catheter.

15. A unit of the type claimed in claim 12 wherein said sheet material container is heat sealed by a transverse line having a length less than the distance between said two edges to thereby restrain said catheter in a predetermined location in said second chamber but permit fluid flow into all of said second chamber.

16. A unit of the type claimed in claim 15 wherein said line emanates from one edge.

17. A unit of the type claimed in claim 16 wherein said line is medially located and does not contact either edge.

18. A unit of the type claimed in claim 1 wherein said guide means is provided with an intermediate enlargement and a cooperating configuration in said restricted portion for retaining said guide means in substantially fixed predetermined orientation relative to said container.

19. An aseptic urethral catheterization unit including an elongated flexible sheet material container sealed on all edges and at each end, a urethral catheter having a predetermined diameter throughout a substantial portion of its length and a hollow open end bulbous portion at one end and port means communicating with the interior bore of the catheter at the opposite end, said catheter positioned within said container, frangible means extending transversely of said container adjacent to one end thereof for providing access to the interior of said container, restricted opening means spaced from said frangible means and forming a first chamber adjacent said one end of said container and a second larger chamber adjacent the second end of said container, said catheter initially being positioned in said second chamber, said restricted opening having an axial passageway capable of accepting said predetermined diameter catheter therethrough, and opener means positioned adjacent to said frangible means for bowing the sheet material walls of said container forming said first chamber into opened position.

20. A unit of the type claimed in claim 19 wherein said first chamber contains resilient opener means initially compressed into a generally flattened condition within said chamber when said container is sealed and released upon fracture of said frangible means to bow the sheet material walls of said container forming said first chamber into an open ended chamber.

21. A unit of the type claimed in claim 20 wherein said opener means is a resilient plastic tubular member capable of being generally flattened for insertion into said first chamber and so constrained when sealed therein, said tubular member having the property of returning to substantially its initial configuration prior to flattening when released from its constrained position.

22. A unit of the type claimed in claim 21 wherein said tubular member is initially substantially cylindrical in cross section and has an axial extent that covers a substantial portion of the axially extending walls forming said first chamber.

23. A unit of the type claimed in claim 19 wherein said opener means includes at least one flat strip-like member having one substantially continuous surface fixed to said container adjacent said frangible means and relieved on the opposite surfaces to facilitate bowing of said member and the container into an open position upon application of forces at opposite ends of said opener means.

24. A flexible plastic container opener adapted for use with a flexible sheet material container having sealed edges and at least one opening formed by adjacent unsealed edges of juxtaposed sheets, said opener including opening means for spreading said sheets into bowed position comprising secondary strip means fastened to said sheet means along one surface of said strip, relief means disposed on the opposite surface of said opener means whereby application of force against opposite ends of said strip causes said sheet material to bow outwardly away from each other.

25. An opener of the type claimed in claim 24 wherein said sheet material has a predetermined thickness and said opener strip has a substantially greater thickness.

26. An opener of the type claimed in claim 25 wherein said sheet material container is polygonal in shape and closed along all edges except one, said strip has a length substantially equal to said open edge and has a width less than said length, one surface of said strip being substantially continuous and in intimate fastened relation to said sheet material adjacent said edge, the opposite surface of said opener being relieved by a plurality of spaced slot means extending between opposite elongated edges of said strip and said slot means penetrating said strip less than the total thickness of said strip.

27. An opener of the type claimed in claim 26 wherein said strip is secured to the exterior surface of said container.

28. An opener of the type claimed in claim 27 wherein said strip is adhesively fastened to said container.

29. An opener of the type claimed in claim 27 wherein said strip is heat sealed to said container.

30. An opener of the type claimed in claim 27 wherein said strip is sonically welded to said container.

31. A method for intermittent catherization of a male patient including the steps of providing an elongated initially sealed flexible imperforate container, a urethral catheter having a predetermined diameter through a substantial portion of its length positioned in said container, said container including elongated flat flexible imperforate sheet material sealed about its entire perimeter in face to face relation, said container having a restricted portion forming a passageway spaced from one end thereof formed by sealing a limited area of said sheet material in face to face relation thereby creating a first chamber between said restricted portion and said one end, a second chamber substantially larger than said first chamber being formed between said restricted portion and said opposite end, substantially all of said catheter being initially positioned within said second chamber in an asceptic fashion but adapted for movement through said passageway upon manipulation externally of said container, said catheter having an eye adjacent one end communicating with the axial bore of said catheter, means for initially maintaining said eye end of said catheter substantially within said passageway which communicates between said chambers, and a transversely disposed weakened portion positioned between said one end and said restricted portion, said weakened portion having a generally linear configuration and existing in substantially aligned relation in each independent layer of said sheet material, said aligned portion extending substantially across the entire width of said container between opposite edges on a line spaced from said one end, manually tearing the container along said line to expose said eye end of said catheter and said first chamber in the interior of said container, applying a surgical lubricant into said first chamber adjacent said restricted portion passageway to thereby substantially seal the juncture of said catheter and said passageway and protect said second chamber against external contamination, inserting the penis glans within said first chamber with said urethra being positioned coaxially with said passageway, feeding said catheter into said urethra until its eye end is positioned within the bladder of the patient to thereby commence evacuation of a fluid specimen through said catheter into said second chamber, restraining said catheter against movement relative to the urethra and the bladder and simultaneously removing said catheter from said container by axial movement through the passageway in said restricted portion and out of the container by movement through said first chamber, introducing an irrigation material into the end of said catheter opposite said eye end to thereby irrigate the patient's bladder and thereafter collect the irrigation material in a secondary container.

32. The method as described in claim 31 wherein a medicament is added to the irrigation fluid prior to introduction into the patient's bladder through said implanted catheter.

33. The method as described in claim 32 wherein a medicament is substituted for the irrigation fluid and inserted directly into the patient's bladder via the catheter.

* * * * *